(12) United States Patent
Bellemare et al.

(10) Patent No.: US 8,303,907 B2
(45) Date of Patent: Nov. 6, 2012

(54) BIOSENSORS, AND METHOD AND KITS FOR USING SAME

(75) Inventors: François Bellemare, Trois-Rivières (CA); Nathalie Boucher, Trois-Rivières (CA); Lucie Lorrain, Champlain (CA)

(73) Assignee: Labbell Inc., Trois-Rivières (CA)

( * ) Notice: Subject to any disclaimer, the term of this patent is extended or adjusted under 35 U.S.C. 154(b) by 0 days.

(21) Appl. No.: 12/764,368

(22) Filed: Apr. 21, 2010

(65) Prior Publication Data

US 2010/0279420 A1 Nov. 4, 2010

Related U.S. Application Data

(63) Continuation of application No. 10/535,825, filed as application No. PCT/CA03/01815 on Nov. 20, 2003, now abandoned.

(30) Foreign Application Priority Data

Nov. 20, 2002 (CA) ..................................... 2412206

(51) Int. Cl.
*B01L 3/00* (2006.01)
(52) U.S. Cl. ........................................................ 422/430
(58) Field of Classification Search ................ 422/61, 422/430
See application file for complete search history.

(56) References Cited

U.S. PATENT DOCUMENTS

| | | | |
|---|---|---|---|
| 4,981,690 A * | 1/1991 | Lopez-Berestein et al. .. | 424/422 |
| 5,389,378 A * | 2/1995 | Madden ........................ | 424/450 |
| 6,121,053 A | 9/2000 | Kolber et al. | |
| 2006/0147342 A1 | 7/2006 | Bellemare et al. | |

FOREIGN PATENT DOCUMENTS

| | | |
|---|---|---|
| CA | 03/01815 | 6/2004 |
| CA | 2506911 | 6/2004 |
| EP | 1134585 | 9/2001 |
| EP | 01830148 | 9/2002 |
| EP | 03776713.4 | 8/2005 |
| WO | WO 2004/046717 A1 | 6/2004 |

OTHER PUBLICATIONS

Ford, R.C.; Barber, J. "Incorporation of sterol into chloroplast thylakoid membranes and its effect on fluidity and function," Panta, 1983, 158, pp. 35-41.*

Enz, C.; Steinkamp, T.; Wagner, R. "Ion Channels in the thyloakoid membrane (a patch-clamp study)." Biochmimca et Biophyisca Acta, 1993, 1143, pp. 67-76.*

(Continued)

*Primary Examiner* — Bobby Ramdhanie
(74) *Attorney, Agent, or Firm* — Goudreau Gage Dubuc; Julie Gauvreau

(57) ABSTRACT

A stabilized thylakoid membrane formulation comprising thylakoid membranes in a buffered solution and liposomes, wherein the formulation has a ratio of chlorophyll/liposomes of at least about 10:1. The invention further comprises a method for detecting or quantifying the presence of toxic molecules in a fluid sample, comprising obtaining a stabilized thylakoids membranes formulation; and assessing the photosynthetic efficiency of the thylakoid membranes formulation in the presence of said sample, whereby the molecules are detected when the photosynthetic efficiency is measurably different in the presence versus in the absence of the sample. The present invention also comprises kits using the stabilized thylakoid membranes formulation for detecting and/or quantifying the toxic molecule in a fluid sample.

19 Claims, 16 Drawing Sheets

OTHER PUBLICATIONS

Bungard et al., "Unusual carotenoid composition and a new type of xanthophyll cycle in plants", Proc. Natl. Acad. Sci., (1999) vol. 96: 1135-1139.
Burkey et al., "Effects of natural shade on soybean thylakoid membrane composition", Protosynthesis Research (1996) 50: 149-158.
Conrad et al., "Changes in yield of in-vivo fluorescence of chlorophyll as a tool for selective herbicide monitoring" J. Appl. Phycol., (1993), 5: 505-516.
Eastman et al., "Changes of the photosystem 2 activity and thylakoid proteins in spruce seedlings during water stress", Photosynthetica (1997) 34(2): 201-210.
Enz et al., "Ion channels in the thylakoid membrane (a patch-clamp study)", Biochimica et Biophysica Acta, (1993) 1143: 67-76.
Ford et al., "Incorporation of sterol into chloroplast thylakoid membranes and its effect on fluidity and function", Planta (1983), 158: 35-41.
Hincha et al., "Proteins from frost-hardy leaves protect thylakoids against mechanical freeze-thaw damage in vitro", Planta (1990) 180: 416-419.
Jay et al., "A high-sensitivity chlorophyll fluorescence assay for monitoring herbicide inhibition of photosystem II in the chlorophyte *Selenastrum capricornutum*": Comparison with effect on cell growth, Arch. Hydrobiol., (1997), 140 (2): 273-286.
Koblizek et al., "A Biosensor for the Detection of Triazine and Polylurea Herbicides Designed Using Photosystem II Coupled to a Screen-Printed Electrode" Biotechnol. Bioeng., (2002), 78 (1): 110-116.
LaBerge et al., "In vitro phytotoxicity screening test using immobilized spinach thylakoids" Env. Tox. Chem., (1999), 18 (12): 2851-2858.
LaBerge et al., "Comparative study of thylakoid membranes sensitivity for herbicide detection after physical or chemical immobilization", Enz. Microb. Technol., (2000), 26: 332-336.
Loranger et al., "A fast Bioassay for Phytotoxicity Measurement Using Immobilized Photosynthetic Membranes", Biotechnology and Bioengineering, (1994) 44: 178-183.
Millner et al., "Lipid enrichment of thylakoid membranes", Biochimica et Biophysica Acta, (1983) 722: 331-340.
Ministère De L'Environnement Du Québec, "Critères de la qualité de l'eau de surface au Québec. Direction des écosystèmes aquatiques" Ministère de l'Environnement, Québec, (2001).
Murphy, Denis J., "Reconstitution of energy transfer and electron transfer between solubilised pigment-protein complexes from thylakoid membranes. The role of acyl lipids", Phytosynthesis Research, (1986), 8:219-233.
Porra et al., Determination of accurate extinction coefficients and simultaneous equations for assaying chlorophylls a and b extracted with four different solvents: verification of the concentration of chlorophyll standards by atomic absorption spectroscopy, Biochimia Biophysica Acta, (1989), 975: 384-394.
Rouillon et al., "Amperometric activity measurements of photosynthetic material immobilized in poly (vinylalcohol)-SbQ Application to detect pollutants" Curr. Topics Electroch., (2000), 7: 125-133.

* cited by examiner

BIOSENSORS, AND METHOD AND KITS FOR USING SAME

CROSS REFERENCE TO RELATED APPLICATIONS

This application is a continuation application of U.S. patent application Ser. No. 10/535,825 filed Nov. 14, 2005, now abandoned, which is a National Entry Application of PCT application no. PCT/CA2003/001815 filed on Nov. 20, 2003 and published in English under PCT Article 21(2), which itself claims benefit of Canadian application no. 2,412, 206 filed on Nov. 20, 2002. All documents above are incorporated herein in their entirety by reference.

FIELD OF THE INVENTION

The present invention relates to biosensors, and method and kits for using same. More specifically, the present invention is concerned with photosynthesis-based biosensors, and method and kits for using same.

BACKGROUND OF THE INVENTION

Many assays for detecting toxic molecules in effluents are inefficient when these molecules are present at very low concentration. Assays that are efficient for this purpose such as those made with living organisms and cells like algaes, daphneas, trouts, hepatocytes, or worms are time consuming (up to 72 hours). These methods investigate the presence of toxic molecules in water by measuring the survival of these organisms and cells in contact of the water being tested.

Assays using the response of photosynthetic organs to toxic molecules have been recently devised which in addition to reducing the response time of the assay to 10 minutes are advantageously sensitive to molecules affecting photosynthetic electron transport and simple to use. Thylakoids are the organs responsible for photosynthesis in phytoplankton, algaes and higher plants. In these assays, the physiological response of thylakoids to stress such as toxic molecules is assessed through indirect measurement of photosynthesis, based on a functional relationship between photosynthetic efficiency and a stimulated fluorescence signal. Fluorescence emission by these organs is due to their ability to use light for photosynthesis. Certain methods determine photosynthetic activities from isolated Photosystem II (PS II). For instance, EP patent no. 1,134,585 published on Sep. 19, 2001 in the name of Giardi et al. describes the use of PS II isolated from thylakoids membranes to monitor herbicides. Other methods determine photosynthetic activities of whole plants. For instance, U.S. Pat. No. 6,121,053 issued on Sep. 19, 2000 in the name of Kolber et al. describes a pulsed fluorometer permitting the measurement of photosynthesis efficiency in plants, phytoplankton and algaes. In Laberge (1999) and (2000) are described thylakoids chemically immobilised in a BSA-glutaraldehyde matrix or encapsulated in poly(vinylalcohol) bearing styrylpyridinium substituent groups, respectively.

None of these systems have been demonstrated to be stable at room temperature.

Other methods have used thylakoid membranes themselves which also degrade disadvantageously rapidly at room temperature. These thylakoids samples must be kept at 4° C. and even then only survive a few hours (Table 2). The need to keep the isolated thylakoid membranes at low temperature until immediately before the assay makes their use in in situ assays difficult.

An object of the present invention is therefore to provide improved photosynthesis-based biosensors and bioassays for detecting toxic molecules in fluids, and methods and kits for using same.

SUMMARY OF THE INVENTION

The present invention provides assays using the response of photosynthetic organs to toxic molecules having an advantageously low response time that may be as low as 10 minutes for herbicide detection, 15 minutes for fast toxicity screening or monitoring (as optimised for cation detection), 15 to 180 minutes, depending on the sample tested for effluent toxicity detection ($IC_{50}$ sensitivity).

The biosensors methods and kits of the present invention permit to determine the level/presence of certain toxic molecules in fluids including effluents. These biosensors are sensitive to molecules that affect the photosynthetic electron transport. Molecules that can compete with active sites of photosynthetic enzymes and those that have oxydo-reductive properties can therefore be detected with the methods and bioassays of the present invention.

More specifically, in accordance with the present invention, there are provided biosensors comprising stabilised thylakoid membranes lasting at least about 7 days at room temperature, in specific embodiments about 11 days, and in more specific embodiments about 12 days.

There is also provided a method for detecting toxic molecules comprising the use of these biosensors in combination with a fluorometer advantageously permitting the use of microprocessor since the measurement is made with a non-modulated light rather than pulsed light. The pulsed light permits the measurement of photochemical and non photochemical parameters in the whole plants or algaes. In isolated thylakoid membranes, because certain non photochemical parameters can not be obtained, pulsed light may not be necessary. Furthermore, pulsed light fluorometers are relatively complex, costly and bulky apparatuses. Fluorometers using non-modulated light do not have these drawbacks and are nevertheless able to adequately measure the photosynthetic efficiency of thylakoid membranes.

There is also provided a stabilised thylakoid membrane formulation comprising thylakoid membranes in a buffered solution and liposomes, wherein the formulation has a ratio of chlorophyll/liposomes of at least about 10:1. In a specific embodiment, the buffered solution has a pH between about 6.2 and about 7.8. In an other specific embodiment, the formulation has a ratio of chlorophyll/liposomes of between about 10:1 and 100:1. In an other specific embodiment, the formulation may further comprise polyvinylpyrrolidine (PVP) in a concentration lower than about 4% v/v. The liposomes in formulation may be constituted of phosphatidylcholine and phosphatidylglycerol in a ratio of about 10:1.

There is also provided a kit for detecting a toxic molecule in a fluid comprising a stabilised thylakoids membranes formulation comprising thylakoids membranes in a buffered solution and liposomes, wherein the ratio of chlorophyll/liposomes is of at least about 10:1; and a portable fluorometer using non-modulated light. In a specific embodiment, the buffered solution has a pH between about 6.2 and about 7.8. In an other specific embodiment, the formulation has a ratio of chlorophyll/liposomes of between about 10:1 and 100:1. In an other specific embodiment, the formulation may further comprise polyvinylpyrrolidine (PVP) in a concentration lower than about 4% v/v. The liposomes in formulation may be constituted of phosphatidylcholine and phosphatidylglycerol in a ratio of about 10:1.

There is also provided a use of a stabilised thylakoid formulation according to the present invention for detecting or quantifying the presence of a toxic molecule in a fluid sample. In a specific embodiment, the toxic molecule is selected from the group constituted of herbicides, and metal cations.

There is also provided method for detecting or quantifying the presence of toxic molecules in a fluid sample, comprising obtaining a stabilised thylakoids membranes formulation according to the present invention; and assessing the photosynthetic efficiency of the thylakoid membranes formulation in the presence of said sample, whereby said molecules are detected when said photosynthetic efficiency is measurably different in the presence versus in the absence of said sample. In a specific embodiment, the photosynthetic efficiency is assessed with a fluorometer using non-modulated light after the thylakoid membranes formulation has been incubated with the sample for a time sufficient to enable any toxic molecules in the sample to disrupt the photosynthetic efficiency of the thylakoid membranes formulation. In an other specific embodiment, the molecules comprise a herbicide and the photosynthetic efficiency assessment is conducted after the thylakoid membranes formulation has been incubated for 10 minutes. In an other specific embodiment, the molecules comprise a metal cation and wherein the photosynthetic efficiency assessment is conducted after 15 to 180 minutes.

There is further provided a method of stabilising thylakoid membranes for use in bioassays comprising mixing thylakoid membranes in a buffered solution with liposomes to yield a thylakoid membranes formulation, whereby the final ratio of chlorophyll/liposomes in the formulation is of at least about 10:1. In a specific embodiment, the buffered solution has a pH between about 6.2 and about 7.8. In an other specific embodiment, the formulation has a ratio of chlorophyll/liposomes of between about 10:1 and 100:1. In an other specific embodiment, the formulation may further comprise polyvinylpyrrolidine (PVP) in a concentration lower than about 4% v/v. The liposomes in formulation may be constituted of phosphatidylcholine and phosphatidylglycerol in a ratio of about 10:1.

In accordance with the present invention, there is therefore also provided a kit for detecting a toxic molecule comprising thylakoids stabilised with liposomes and PVP. In a specific embodiment, the kit further comprises a portable fluorometer using non-modulated light.

The terminology "toxic", "toxic molecule" and "toxicity" refers herein to the property of a substance enabling it to disrupt (inhibit or enhance) in part or in whole the photosynthetic efficiency of thylakoid membranes.

The terminology "photosynthetic efficiency" refers herein to the correlation between the chlorophyll fluorescence and the photochemical reactions (for instance oxygen evolution).

The terminology "sample" refers herein to any fluid containing toxic molecules. Without being so limited, it includes surface water, ground water, storm water, underground water, drinking water, agricultural effluents, industrial effluents (pulp and paper, municipal waste water, waste water landfills leachates, textile, petrochemical, chemical, mining), water extracted from food, sludge, sediments, scories, etc.

Fluorescence

A number of parameters are used to measure the fluorescence emitted by thylakoid membranes. $F_0$ corresponds to the minimal fluorescence of the activated photosystems. This fluorescence is produced by a weak illumination of the photosystems. $F_1$ corresponds to an illumination slightly higher than $F_0$. $F_2$ (near maximal fluorescence level) corresponds to the fluorescence produced by strong/actinic illumination.

Other objects, advantages and features of the present invention will become more apparent upon reading of the following non-restrictive description of preferred embodiments thereof, given by way of examples only with reference to the accompanying drawings.

The present description refers to a number of documents, the content of which is herein incorporated by reference in their entirety.

DESCRIPTION OF SPECIFIC EMBODIMENTS

The present invention is illustrated in further detail by the following non-limiting examples.

EXAMPLE 1

Fluorometer

In a specific embodiment, a fluorometer continuously illuminates weakly the photosynthetic biological material with a light emitting diode (LED) emitting light at a wavelength of 475 or at 660 nm. Better results were obtained with the 475 nm wavelength. In order to obtain a higher sensitivity for measuring the photosynthetic response to toxic molecules, the intensity of the low excitation light was adjusted so as to obtain a $F_1$ fluorescence level slightly higher than $F_0$.

Figure 1:
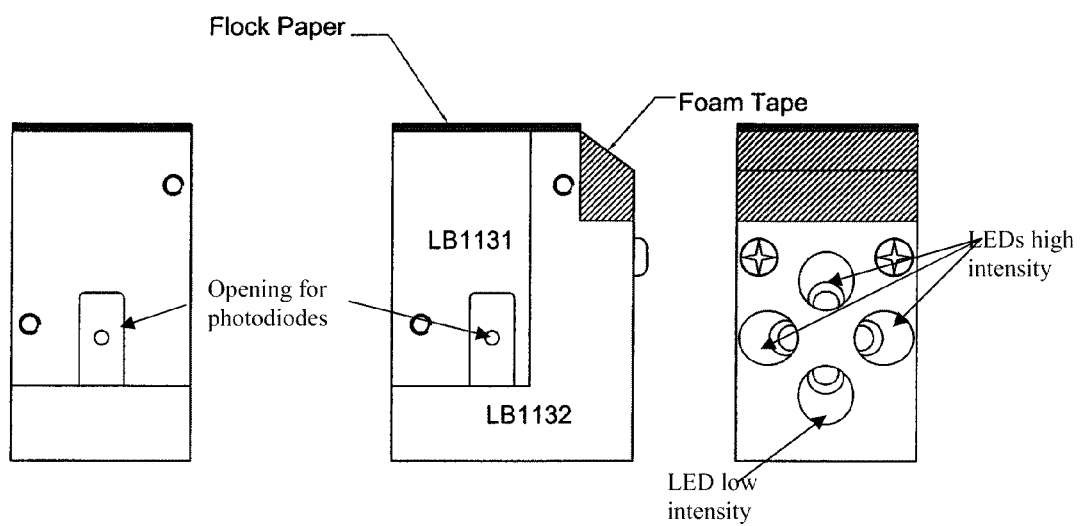
FIG. 1 schematically illustrates the disposition of LEDs in a fluorometer according to a specific embodiment of the present invention.

Fluorescence measured 2 sec after turning on one LED is $F_1$. Three additional LEDs are then turned on so as to induce actinic illumination $F_2$. Dispersion of LEDs is illustrated in FIG. 1. Light beams are oriented so as to form together a point of convergence precisely at the level where the photodiode is read. After a specific time, selected according to the nature of the thylakoid membranes used (eg. source of thylakoids, etc.) (Table 1), of the background noise and of the level of sensitivity sought, the $F_2$ fluorescence is measured. To determine $F_1$ and $F_2$, the fluorometer measures wavelengths higher than 650 nm when the illumination is at 475 nm, and higher than 700 nm when illumination is at 660 nm.

TABLE 1

Influence of time delay on the fluorescence levels ($F_1$ and $F_2$) and the photosynthetic efficiency of stabilised thylakoid membranes

| Delay (msec) | $F_1$ | $F_2$ | Photosynthetic Efficiency |
|---|---|---|---|
| 10 | 292 966 | 1 671 640 | 0.827 |
| 50 | 295 358 | 1 216 677 | 0.757 |
| 200 | 299 277 | 908 464 | 0.669 |
| 1 000 | 289 175 | 707 659 | 0.591 |

Figure 2:
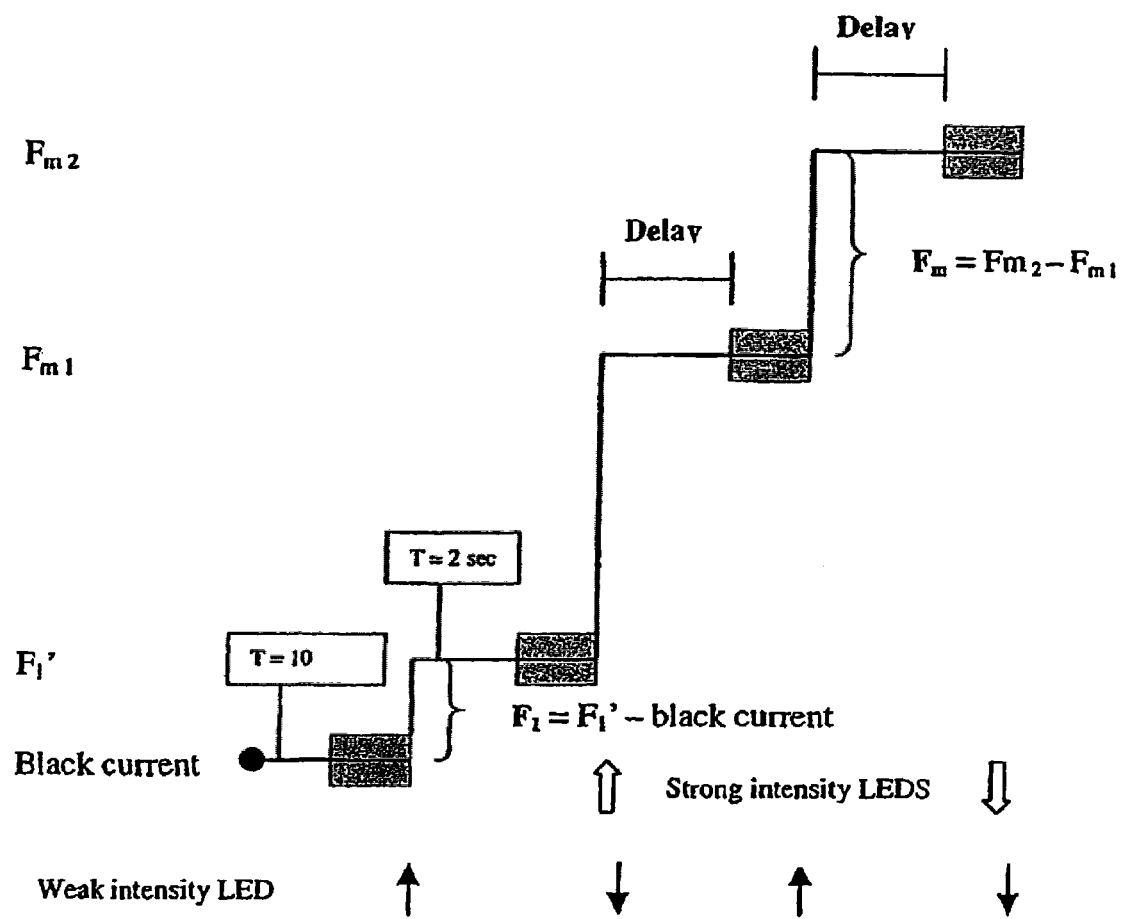
FIG. 2 schematically illustrates the measurement mode of a fluorometer according to a specific embodiment of the present invention.

FIG. 2 illustrates how fluorescence measurements are collected and how the fluorometer may be adjusted according to a specific embodiment of the present invention. The terminology "gain" is used to refer to the signal integration varying as selected from 0.32 to 80 msec. The terminology "Delay" is used in this figure to refer to the delay of 0.1 to 1000 msec required by LEDs in order to produce the actinic illumination after their activation. The specific delay is adjusted in light of the various parameters listed with regards to the delay before reading. The terminology "strong intensity" is used to refer to the current applied to LEDs to produce a variation in the light intensity between 2 and 20 mV ($F_2$ reading). The terminology "weak intensity" is used to refer to the current applied to the LED to produce a variation in the light intensity between 0 and 1.6 mV ($F_1$ reading).

The photosynthetic efficiency is determined with the following formula $(F_2-F_1)/F_2$. Preferably, the photosynthetic efficiency of the stabilised thylakoids is 0.8±0.1. Any molecule affecting the photosystems modifies either $F_1$ or $F_2$ which modification necessarily disrupts (increases or decreases) the photosynthetic efficiency. The inhibition curve of a particular molecule is determined by calculating the activity of the photosystems in the absence of the molecule and in the presence of the molecule and comparing both efficiency as follows as described in Conrad 1993:

Without inhibitor (wi):

$$\text{efficiency}_{(wi)} = (F_{2(wi)} - F_{1(wi)})/F_{2(wi)}$$

With inhibitor:

$$\text{Relative photosynthetic efficiency}_{(sample)} = (F_{2(sample)} - F_{1(sample)})/F_{2(wi)}$$

Percentage efficiency:

$$\text{efficiency (\%)} = (\text{efficiency}_{(sample)} \times 100)/\text{efficiency}_{(wi)}$$

Percentage inhibition:

$$\text{Inhibition (\%)} = 100 - \text{efficiency (\%)}$$

The person of ordinary skill in the art will understand that any fluorometer may be used in accordance with the present invention. Hence modulated light fluorometers are also within the scope of the present invention.

EXAMPLE 2

Preparation of Thylakoid Membranes

All steps are conducted in the dark or under green light and at cold temperature (samples on ice or procedure in cold room). Thylakoid membranes are isolated from 100 g of deveined spinach leaves. Spinach leaves are then crushed in a mixer with homogenising a buffer comprising TES-NaOH 20 mM pH 7.5, sorbitol 330 mM and $MgCL_2$ 5 mM. Other conventional buffers could be used including TES, Hepes, Tris, phosphate, tricine and MOPs. The homogenate is filtered on a cheese cloth and the filtrate is centrifuged 2 min at 2500×g at 4° C. on a Eppendorf™ 5810-R, rotor # A-4-44.

The pellet is then resuspended in a hypotonic solution consisting in 1 in 20 of the homogenising buffer. This step is used to lyse the chloroplast membranes. The resulting solution is then crushed in a Wheaton™ mixer and centrifuged 3 min. at 3500×. The resulting pellet contains the purified membranes. They are then resuspended in a buffer consisting of TES-NaOH 20 mM pH 7.5, sorbitol 330 mM, $MgCL_2$ 5 mM and $NH_4Cl$ 1 mM to as to obtain a final concentration of chlorophyll/thylakoid membranes between 2 and 3 mg/ml. The chlorophyll concentration is assessed according to the method described in Porra (1989) described herein. The solution is then either stored at −80° C. for later use or may be stabilised for storing at room temperature for short to medium term use.

EXAMPLE 3

Preparation of Ready to Use Stabilised Thylakoid Membranes Formulation

A preparation of 2 to 3 mg/mL of thylakoid membranes were mixed with a pH 6.5 phosphate buffer containing: 0.02 M phosphate, sucrose 300 mM, $NH_4Cl$ 10 mM, $MgCL_2$ 20 mM, EDTA 10 mM, polyvinylpyrrolidine (PVP) (125 μL of solution 20% for 1 mL) and liposomes constituted of phosphatidylcholine and phosphatidylglycerol in a ratio of 10:1 to obtain a solution of 0.0125 mg of liposome/mL of chlorophyll/thylakoid membranes buffered solution. In this stabilised thylakoid membrane formulation, the final concentrations of PVP is of 2% v/v, the final concentration of liposomes is of 0.0125 mg/mL v/v and that of chlorophyll is of 0.125 mg/mL v/v.

The PVP increased the stability of the thylakoid preparations as compared to the same preparation without PVP but a useful stability was nevertheless obtained even without PVP. The amount of PVP may be varied without affecting the stability of the thylakoid membranes between about 0 and about 4% PVP v/v (data not shown). Other conventional buffers at pH ranging between about 6.2 and about 7.8—a variation of about 10% is generated within this pH range (data not shown)—can also be used without affecting the usefulness of the thylakoid preparation of the present invention.

The quantity of liposomes used was determined via the ratio chlorophyll/liposome. This ratio may vary and is preferably at least equal to 10:1 and better results with regards to stability and sensitivity were obtained with a ratio 100:1. Any ratio higher than 100:1 is expected to work. The liposomes are believed to help to the formation of thylakoid membranes vesicle thereby increasing their stability and increasing the consistency of the readings. The quantity used can be varied as long as the final ratio of chlorophyll/liposomes is at least about 10:1.

100 µL of this solution was poured into a 5 mL or 7 mL tube previously refrigerated. The tubes were then frozen and then lyophilised with a Speed-Vac™ from Savant (#SS-22). Lyophilization was conducted 4 hours in order to remove water completely from the 100 µL amount. The tubes are then closed and kept at the desired temperature. Table 2 presents the stability of various thylakoid preparations obtained as a function of the temperature of storage.

TABLE 2

Stability of various thylakoid membranes formulations

| | Conservation time | | | |
|---|---|---|---|---|
| T° | Natives | PVP | PVP (under vacuum) | PVP (under vacuum + liposomes) |
| −80° C. | >5 month | >5 month | >5 month | N.D. |
| −20° C. | >3 month | >3 month | >3 month | N.D. |
| 4° C. | 18 hours | 12 days | >1 month | N.D. |
| 20° C. | 4 hours | 7 days | 11 days | 12 days |
| 37° C. | N.D. | 2 days | 4 days | 4 days |

N.D. = not determined

Table 3 presents the detection sensitivity of thylakoid membranes stabilised according to the method presented herein as well as their median inhibitory concentration ($IC_{50}$) on various herbicides. In some of the thylakoid membranes preparations of the present invention, a detection threshold of 1 ppb was observed with atrazine.

EXAMPLE 4

Preparation of Concentrated Stabilised Thylakoid Membranes Formulation

A concentrated batch of 50 tests was prepared in a total volume of 20 mL of solution constituted of thylakoid membranes at chlorophyll/thylakoid concentration of 0,625 mg/mL, Tes-NaOH 25 mM pH 7.5, HEPES-NaOH 25 mM pH 7.5, sorbitol 330 mM, $MgCl_2$ 2 mM, $NH_4Cl$ 1 mM, PVP 2% (p/v) and liposomes (phosphatidylcholine:phosphatidyglycerol 10:1). 1 mL of this solution was poured in an amber bottle. This preparation can obviously be adapted for the preparation of a smaller or larger number of tests. In this concentrated stabilised thylakoid membrane formulation, the final concentrations of PVP is of 2% v/v, the final concentration of liposomes is of 0.0625 mg/mL v/v and that of chlorophyll is of 0.625 mg/mL v/v. The quantity used can be varied as long as the final ratio of chlorophyll/liposomes is of at least about 10:1.

EXAMPLE 5

Resuspension of Stabilised Thylakoid Membranes

The individual test tubes (100 µL lyophilised thylakoid membranes) were resuspended in 2 mL of water or tested samples. The concentrated batch of test tubes was resuspended in water, in Buffer 1 (HEPES-NaOH 50 mM pH 7.5 buffer containing sucrose 330 mM, $MgCl_2$ 20 mM, $NH_4Cl$ 10 mM, PEG 4000 4% (p/v)); or in Buffer 2 (phosphate buffer 0.1 M pH 6.5 containing sucrose 330 mM, $NH_4Cl$ 10 mM, $MgCl_2$ 20 mM, EDTA 10 mM, PEG 4000 4% (p/v)). A combination of buffered solutions 1 and 2 may also be used. Addition of bicarbonate (10 µg/mL) and hydroxylamine (100 µg/mL) in these buffers did not give statistically difference in the results. These different buffers rs produce different results in the detection sensitivity (see Table 3 above). The final volume obtained depends on the quantity of lyophilised membranes used (2.5 mL for 25 tests, 5 mL for 50 tests).

As may be seen in Table 4 below, thylakoid membranes an detect toxic molecules such as metal cations.

TABLE 3

Detection sensitivity of stabilised thylakoid membranes resuspended in various buffers and median inhibitory concentration ($IC_{50}$) on various herbicides

| | Threshold (mg/L) | | | IC50 (mg/L) | | |
|---|---|---|---|---|---|---|
| Herbicides | Buffer 1 | Buffer 1 + 5 mM MgCl2 (in cuvette) | Buffer 2 | Buffer 1 | Buffer 1 + 5 mM MgCl2 (in cuvette) | Buffer 2 |
| Atrazine | 0.002 | 0.001 | 0.002 | 0.13 | 0.04 | 0.33 |
| Desethyl atrazine | 0.013 | 0.2 | 0.2 | 1.08 | 1.1 | 2.31 |
| Deisopropyl atrazine | 0.2 | >0.1 | 1.26 | >1 | >0.1 | >4 |
| Cyanazine | 0.002 | 0.0006 | 0.013 | 0.009 | 0.028 | 0.135 |
| Simazine | 0.002 | 0.06 | | 0.028 | 0.942 | |
| Diuron | 0.0006 | 0.002 | <0.001 | 0.022 | 0.011 | 0.02 |
| Propanil | 0.002 | 0.0006 | 0.013 | 0.179 | 0.068 | 0.221 |
| Bromoxynil | 0.013 | >0.1 | 0.06 | 0.443 | >0.1 | 0.414 |
| Bentazon | 2 | >4 | 1.22 | >4 | >4 | >4 |

$IC_{50}$ = concentration required to produce 50% inhibition of efficiency

TABLE 4

Detection sensitivity of stabilised thylakoid membranes and median inhibitory concentration ($IC_{50}$) on various metal cations

| Metals Incubation time (min) | Threshold limit value (mg/L) | $IC_{50}$ (mg/L) |
|---|---|---|
| As | | |
| 15 | 61 | >100 |
| 30 | 35 | 74 |
| 60 | 16 | 50 |
| Cu | | |
| 15 | 0.02 | 0.325 |
| Cd | | |
| 15 | <5 | 87.2 |
| 30 | <5 | 31.7 |
| 60 | <5 | 15.4 |
| Co | | |
| 15 | >100 | >100 |
| 30 | 16 | >100 |
| 60 | <5 | 90 |
| Hg | | |
| 15 | 0.7 | 2.5 |
| 30 | 0.35 | 2.0 |
| 60 | 0.35 | 2.0 |
| Ni | | |
| 15 | 35 | >100 |
| 30 | 7.1 | >100 |
| 60 | 7.1 | >100 |
| Pb | | |
| 15 | 1.6 | >10 |
| 30 | 1.6 | 6.9 |
| 60 | <1.0 | 3.1 |
| Zn | | |
| 15 | 16 | >100 |
| 30 | 16 | 70 |
| 60 | 7.1 | 34 |

The anion combined to the metal in the metal salts used can influence the detection sensitivity (chloride, sulphate, nitrate, carbonate, solutions in nitric acid etc).

EXAMPLE 6

Determination of Thylakoid Membrane Activity by the DCIP Reduction Method

The measurement of photosynthetic efficiency of the stabilised thylakoid membranes according to the methods of the present invention is validated with the dichlorophenol (DCIP) reduction method.

Test tube A: To 750 µL of a blank buffer (Sodium phosphate 0.5 M pH 6.2) or of a lyophilisation buffer (phosphate of sodium 0.5, M pH 6.2 containing EDTA 10 mM; $MgCl_2$ 20 mM; $NH_4Cl$ 10 mM; sucrose 330 mM; PVP 1%), add 500 µL of DCIP solution 3.6 mM, and 500 µL of the thylakoid dispersion (Thylakoid membranes diluted to 17.5 µg/mL$^{-1}$ of chlorophyll with ice-cold blank buffer or lyophilization buffer).

Test tube B: to 750 µL of the blank buffer (buffer (Sodium phosphate 0.5 M pH 6.2) or of the lyophilization buffer (as described above in test tube A), add 500 µL of DCIP solution 3.6 mM and 500 µL of distilled water.

Then read the absorbance at 655 nm for both tubes. Incubate 10 minutes under a 100 W lamp at room temperature and read again the absorbance at 655 nm. The activity is calculated with the following formula: (Reading at 655 nm after illumination)−(reading at 655 nm after illumination).

The results in Tables 5 and 6 below are expressed as DPIP reduction per mg of chlorophyll per hour. Different volumes of DPIP solution are diluted in appropriate volumes of buffer and the absorbance is read at 655 nm.

TABLE 5

Concentration/volume of DPIP used relating to volume of buffer used

| Concentration of DPIP mM | Volume of DPIP 3.6 mM (µL) | Vol. of blank or lyophilised buffer (mL) |
|---|---|---|
| 0 | 0 | 1.75 |
| 0.05 | 103 | 1.65 |
| 0.10 | 206 | 1.54 |
| 0.30 | 309 | 1.44 |
| 0.40 | 412 | 1.34 |
| 0.60 | 618 | 1.13 |
| 0.70 | 721 | 1.03 |
| 0.90 | 927 | 0.82 |

TABLE 6

Absorbance of solution before and after illumination

| Concentration of DPIP mM | Absorbance at 655 nm (before illumination) | Absorbance at 655 nm (after illumination) |
|---|---|---|
| 0 | 0 | 0 |
| 0.05 | 0.125 | 0.125 |
| 0.10 | 0.218 | 0.216 |
| 0.30 | 0.545 | 0.535 |
| 0.40 | 0.875 | 0.871 |
| 0.60 | 1.259 | 1.249 |
| 0.70 | 1.311 | 1.302 |
| 0.90 | 1.878 | 1.874 |
| Sample 0.45; 0.46 | Sample 2.009; 1.932 | Sample 1.145; 0.981 |

The concentrations of DPIP as determined with the fluorescence method of the present invention was compared with the real DPIP values to validate the method of the present invention.

EXAMPLE 7

Measure of Chlorophyll Concentration in Stabilised Thylakoid Membranes

The chlorophyll concentration in the stabilised preparation is measured with a conventional absorbance dosage test. 10 µL of thylakoids extract is added into 5 mL Acetone 80%. The mixture is then centrifuged 5 min on a table centrifuge, and the absorbance is read at 647 nm and at 664 nm on a photometer. The total chlorophyll concentration is then calculated with the following formula as described in Porra (1989):

$$[(17.76 \times A647)] + (7.34 \times A664) \times 500/1000 = mg/mL.$$

The chlorophyll concentration is then adjusted by diluting the preparation with a suitable buffer or water to reach the desired concentration. In a specific embodiment, this concentration is of 5 µg/mL.

EXAMPLE 8

Incubation of Thylakoid Membranes

Before use, the tubes containing stabilised thylakoid membranes were retrieved from storage. If they were stored in the freezer or the refrigerator, they were tempered 30 minutes at room temperature and in the dark. Two milliliters of fluid samples and the required volume of $MgCl_2$ mother solution to get 0-10 mM $MgCl_2$ (depending on tested samples) were added to 100 μL of the thylakoids membranes formulation at a concentration of 5 μg/mL. The tubes are then shook by inversion for 2 min. The tubes were then left in the dark for a further 1) 10 minutes for herbicide detection; or 2) a further 180 minutes for determination effluent toxicity before fluorescence measures were taken.

EXAMPLE 9

Comparison of Sensitivity and Stability at Room Temperature of Photosynthesis-Based Biosensors of the Prior Art with Stabilised Thylakoid Membranes According to the Present Invention

TABLE 7

Comparison of detection sensitivity of photosynthesis-based biosensors of the prior art with that of the present invention

| | Thylakoids | | | | | | |
|---|---|---|---|---|---|---|---|
| | Stal sed thylakoid membranes of the | Chemically | | PSII | | algaes | |
| | present | immobilised | Physically | Screen printed | Clark | | |
| Substance tested | invention (fluorescence) | thylakoids[a] (electrochemistry) | immobilised[d] (electrochemistry) | electrode[b] (electrochemistry) | electrode[b] (amperometry) | native[c] (fluorescence) | native[e] (fluorescence) |
| | | | threshold (mg/L) Detection mode | | | | |
| Atrazine | 0.001 | 0.01-0.05 | N.D. | 0.0004 | 0.0004 | 0.009 | N.D. |
| Diuron | 0.002 | 0.01 | N.D. | 0.0002 | 0.0001 | 0.002 | N.D. |
| | | | $IC_{50}$ (mg/ml) Detection mode | | | | |
| Atrazine | 0.04 | 0.33 | 0.28 | 0.019 | 0.065 | 0.062 | 0.15 |
| Cyanazine | 0.04 | 0.079 | 0.31 | N.D. | N.D. | N.D. | N.D. |
| Diuron | 0.071 | 0.12 | 0.13 | 0.16 | 0.019 | 0.012 | 0.959 |
| 2,4 D | n.d. | >1000 | N.D. | N.D. | N.D. | N.D. | N.D. |
| Metolachlor | n.d. | 580 | N.D. | N.D. | N.D. | N.D. | N.D. |

$T_{1/2}$ = The time required for the photosynthetic activity of the thylakoid membranes to decrease to half of its initial value.
[a]Laberge (1999);
[b]Koblizek, (2002);
[c]Jay (1997);
[d]Laberge (2000);
[e]Conrad (1993);

TABLE 8

Comparison of stability at room temperature of photosynthesis-based biosensors of the prior art with stabilised thylakoid membranes

| Immobilised preparation stability $T\ 1/2$ | Stabilised thylakoid membranes (fluorescence) | Chemically immobilised thylakoids[f] Clark electrode | Physically immobilised[d] (electrochemistry) | Screen printed electrode[b] (electrochemistry) | Clark electrode[b] (amperometry) | native[c] (fluorescence) | native[e] (fluorescence) |
|---|---|---|---|---|---|---|---|
| at 22° C. | >288 hours | 50 hours[f] | 24 hours[b] | 24 hours[b] | No immobilisation | N.D. | N.D. |
| at 4° C. | >720 hours* | 800 hours[f] | 2160 hours*[g] | Not available | Not available | No immobilisation | No immobilisation |

[b]Koblizek, (2002);
[c]Jay (1997);
[d]Laberge (2000);
[e]Conrad (1993);
[f]Loranger (1994);
[g]Rouillon (2000);
*The loss of efficiency of native membranes after lyophilization as compared to that obtained after physical immobilisation is of 20% and 40%, respectively.

EXAMPLE 10

Determination of $IC_{50}$ of Stabilised Thylakoid Membranes with Atrazine

The inhibition data obtained with the method of the present invention permits to determine the initial concentration of the toxic molecule in the sample tested. Hence, as is presented in Table 9 below, from a calculated inhibition of 64.8%, it is possible to calculate a probit of 5.377, which in turn, permits to establish that the sample contained an initial concentration of 4 mg/L of atrazine (Finney, 1971).

TABLE 9

Linear regression Log-Probit values between 5 and 95% effect

| atrazine mg/L | Log(10) Conc. *10 | % effect | probit |
|---|---|---|---|
| 0.1 | 0.000 | 69.4 | 5.502 |
| 0.04 | −0.398 | 55.3 | 5.133 |
| 0.004 | %−1.398 | 14.9 | 3.957 |
| 0.001 | % −2.000 | 4.2 | 3.273 |

Slope (B) = 1.12; Data number = 3; Interception = 5.53; degree of freedom = 1; Variance (S2) = 0.003; standard error = 0.056; Standard error of regression line = 0.033; correlation coefficient ® = 0.9988; correlation coefficient for a confidence of 95% = 0.997; determination coefficient ($R^2$) = 0.9976; regression formula: Y = 5.533 + 1.118 * X; regression formula: X = Y − 5.534/1.118; CI50 = 0.033 mg/L (0.031-0.036); Slope significant value: T = 20.2 dl = 1 p = 0.031454;
This line is significantly different from 0. Its confidence interval can be calculated as 1.118 +/− T(1) * 0.055

EXAMPLE 11

Figure 5:
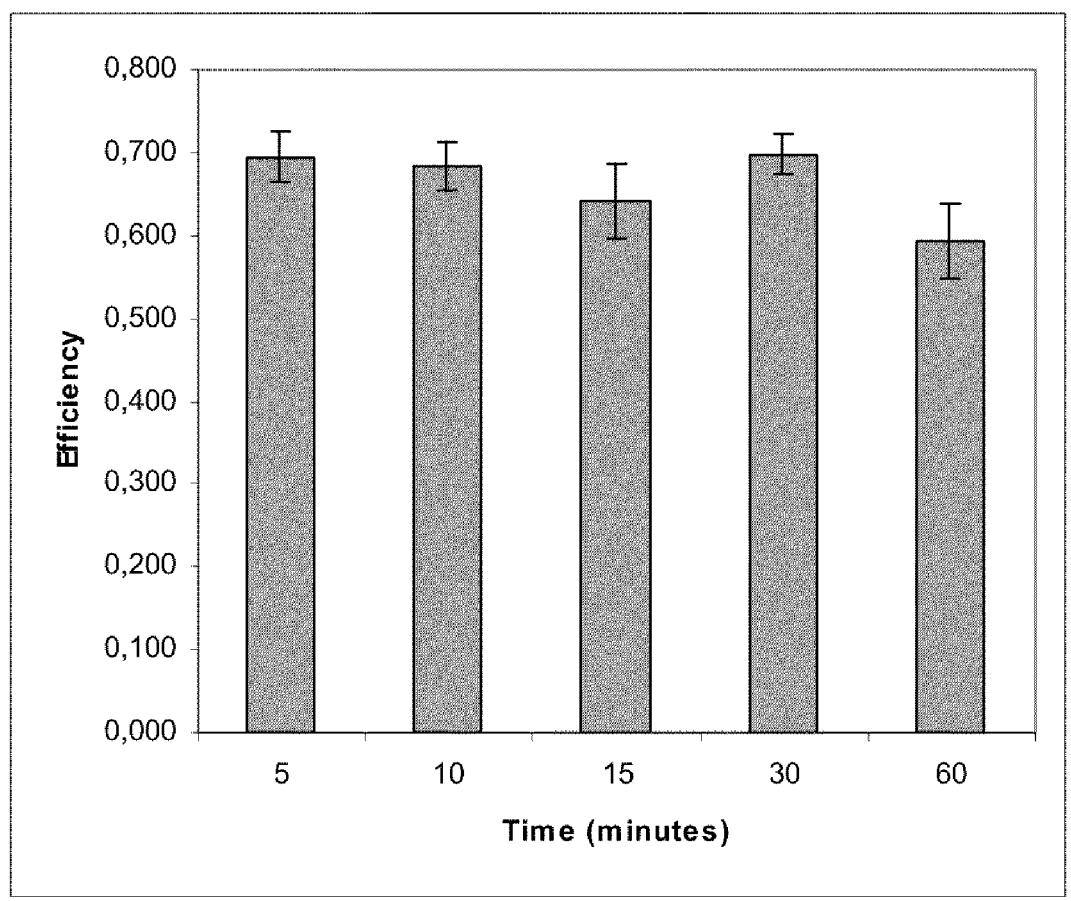
FIG. 5 graphically illustrates the variation of photosynthetic efficiency of stabilised thylakoid membranes according to specific embodiments of the present invention as a function of time after the release of the membranes in a solution.
Figure 6:
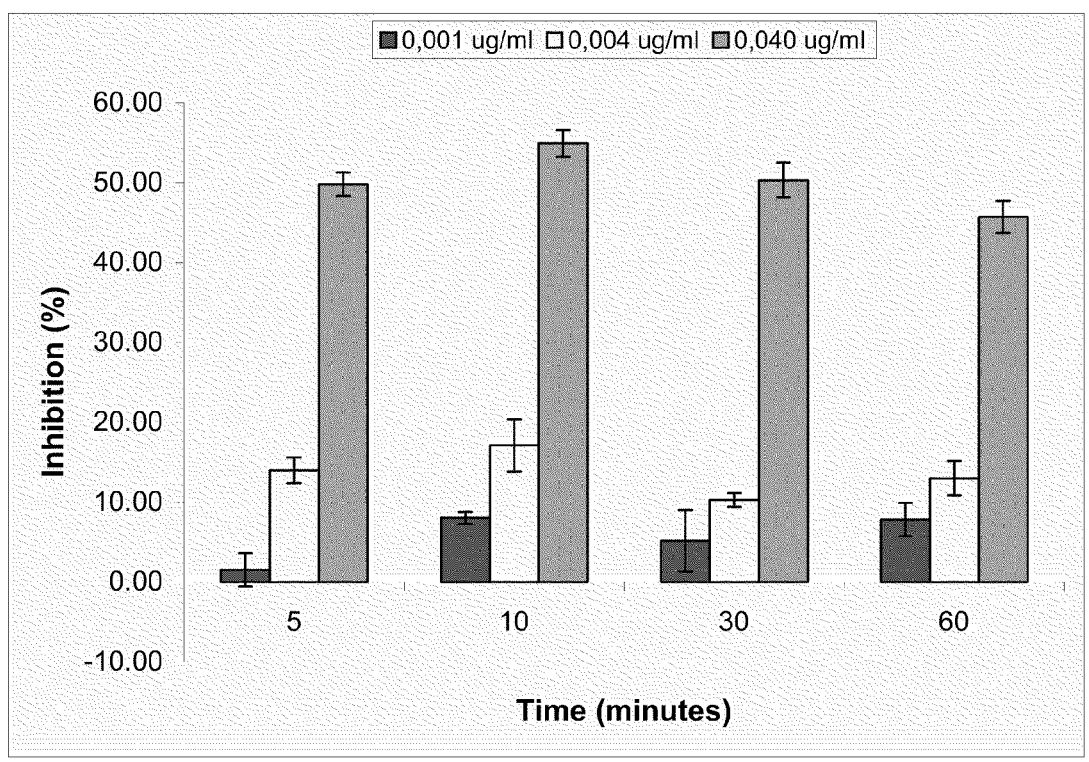
FIG. 6 graphically illustrates the variation of inhibition of the photosynthetic efficiency of stabilised thylakoid membranes as a function of various concentrations of atrazine, and at different times after their release in solution.

Effect of Incubation Time on Fluorescence Emission by Stabilised Thylakoid Membranes for Herbicide Detection The incubation time before taking fluorescence measurement was fixed at ten minutes. Fluorescence emission up to 60 minutes after thylakoids release in solution is substantially similar to that found at ten minutes. It is believed that measuring after less than 10 minutes after release may affect the sensitivity of the tests since a lower concentration of herbicide molecules (FIG. 5) takes more time to inhibit the fluorescence signal.

EXAMPLE 12

Figure 3:
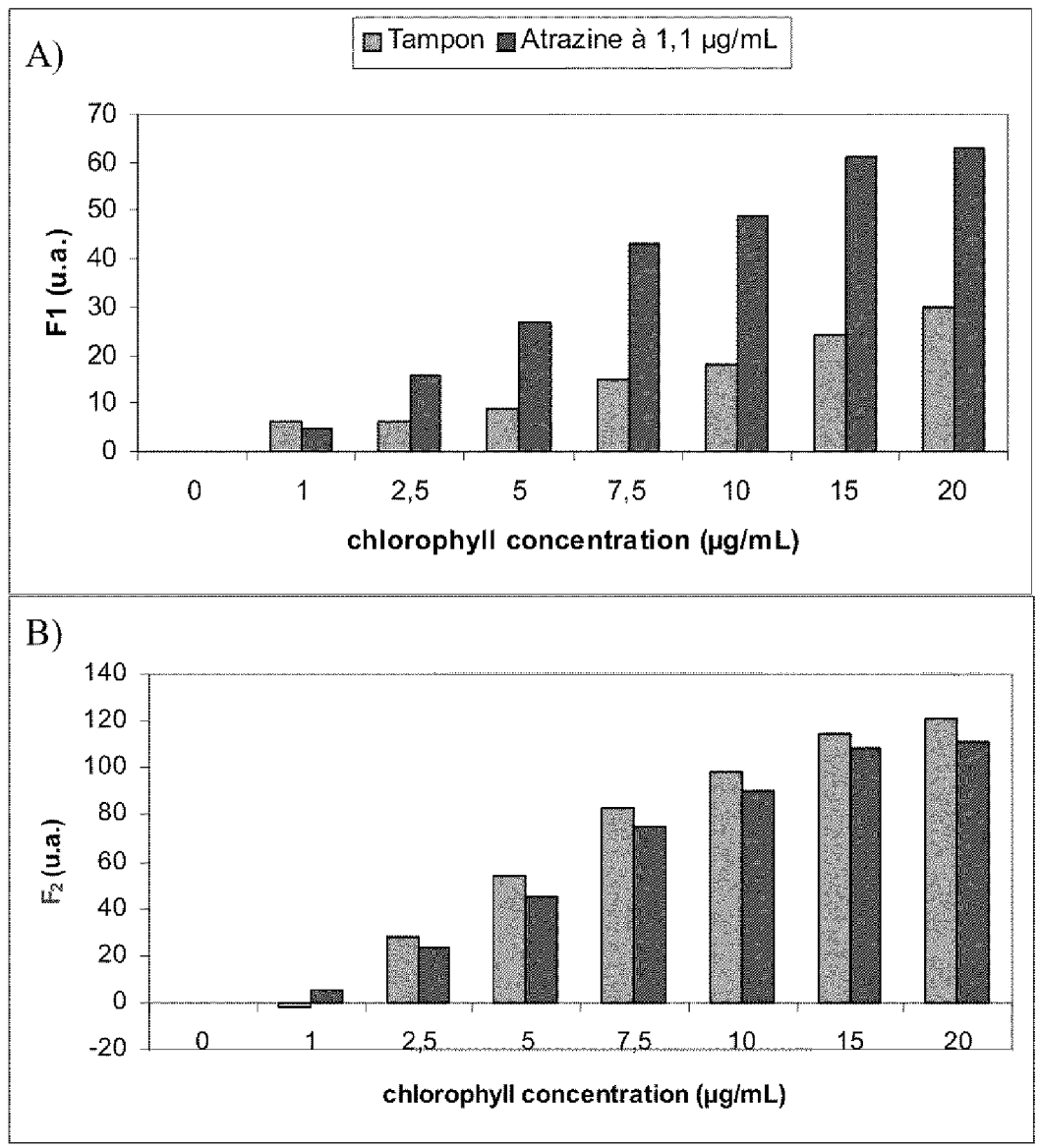
FIG. 3 graphically illustrates the variation of the parameters $F_1(A)$ and $F_2(B)$ as a function of chlorophyll concentration in stabilised thylakoid membranes.
Figure 4:
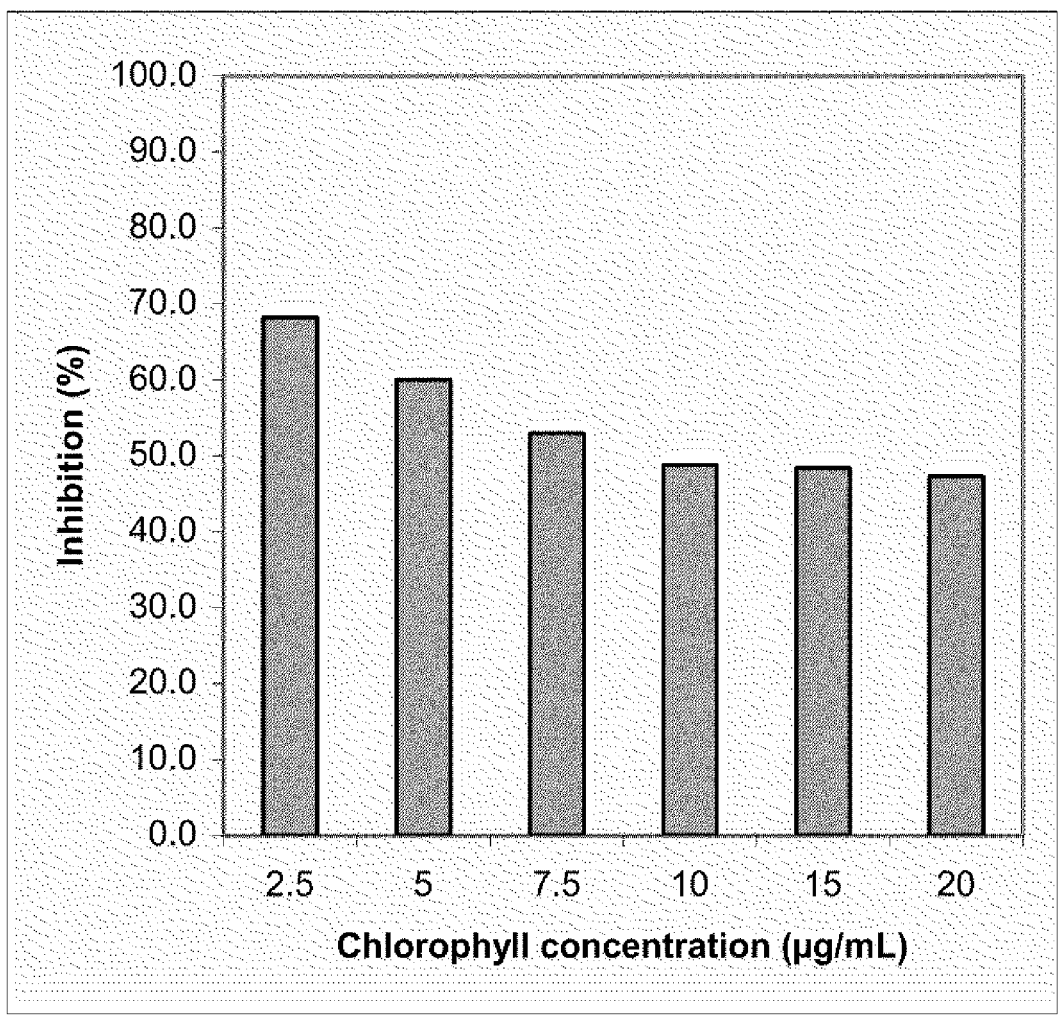
FIG. 4 graphically illustrates the variation of inhibition of the photosynthetic efficiency of stabilised thylakoid membranes by 1.08 µg/mL atrazine according to specific embodiments of the present invention as a function of chlorophyll concentration calculated with the $F_1(A)$ and $F_2(B)$ data presented in FIG. 3.

Effect of Concentrations of Chlorophyll in Stabilised Thylakoid Membranes Preparation on Fluorescence Measurement The variation of the parameters $F_1$ (A) and $F_2$(B) was determined as a function of chlorophyll concentration (FIG. 3) on membranes stabilised with PVP and liposomes as described herein. These measurements determined the lowest effective concentration of membrane thylakoids (expressed as chlorophyll concentration) needed to perform the test. Concentrations between 10 and 20 μg/mL of chlorophyll/thylakoids give almost the same result. Using the lowest chlorophyll/thylakoids concentration possible is desirable to limit the turbidity of the solution caused by chlorophyll which decreases fluorescence. FIG. 4 illustrates that at lower chlorophyll concentrations, better results are obtained.

EXAMPLE 13

Effect of pH on Fluorescence Measurement on Stabilised Thylakoid Membranes

Figure 7:
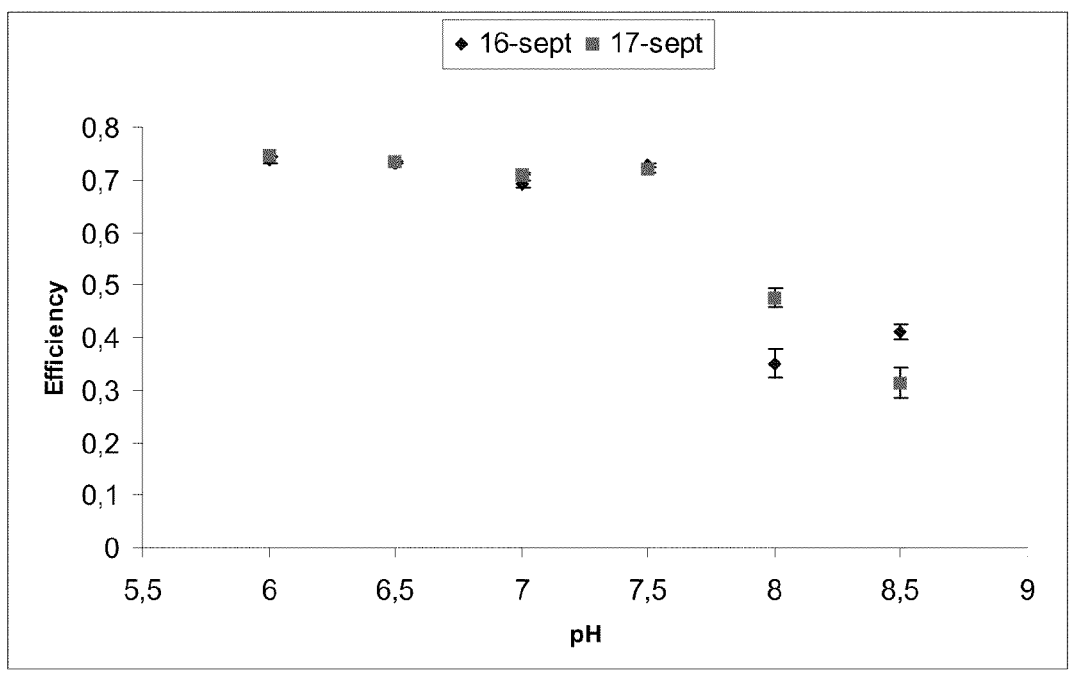
FIG. 7 graphically illustrates the variation of the photosynthetic efficiency of thylakoid membranes as a function of pH.
Figure 8:
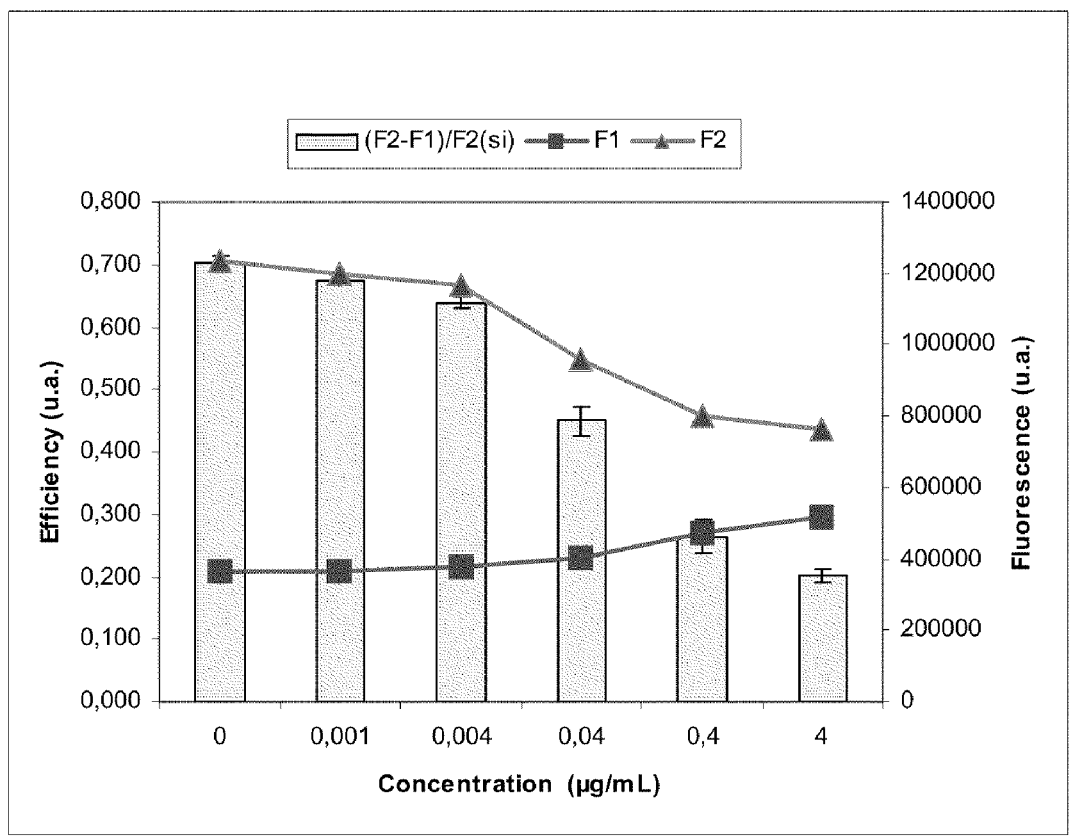
FIG. 8 graphically illustrates the effect of various concentrations of atrazine on fluorescence parameters $F_1$ and $F_2$ and the calculated photosynthetic efficiency with optimal conditions presented in FIGS. 3-7 on stabilised thylakoid membranes which were obtained after optimisation of LEDs installation and defined conditions of light intensity, time duration.

The variation of the photosynthetic efficiency of thylakoid membranes as a function of pH was measured on thylakoids stabilised with PVP and liposomes as described herein. The results presented in FIG. 7 indicate that basic pHs (defined herein as higher than 7.8) inhibit photosynthetic efficiency as do toxic substances. Therefore, in specific embodiments of the method of the present invention, the pH of the aqueous solution is adjusted at 7.5 prior to releasing the thylakoid membranes for fluorescence measurement.

EXAMPLE 14

Figure 9:
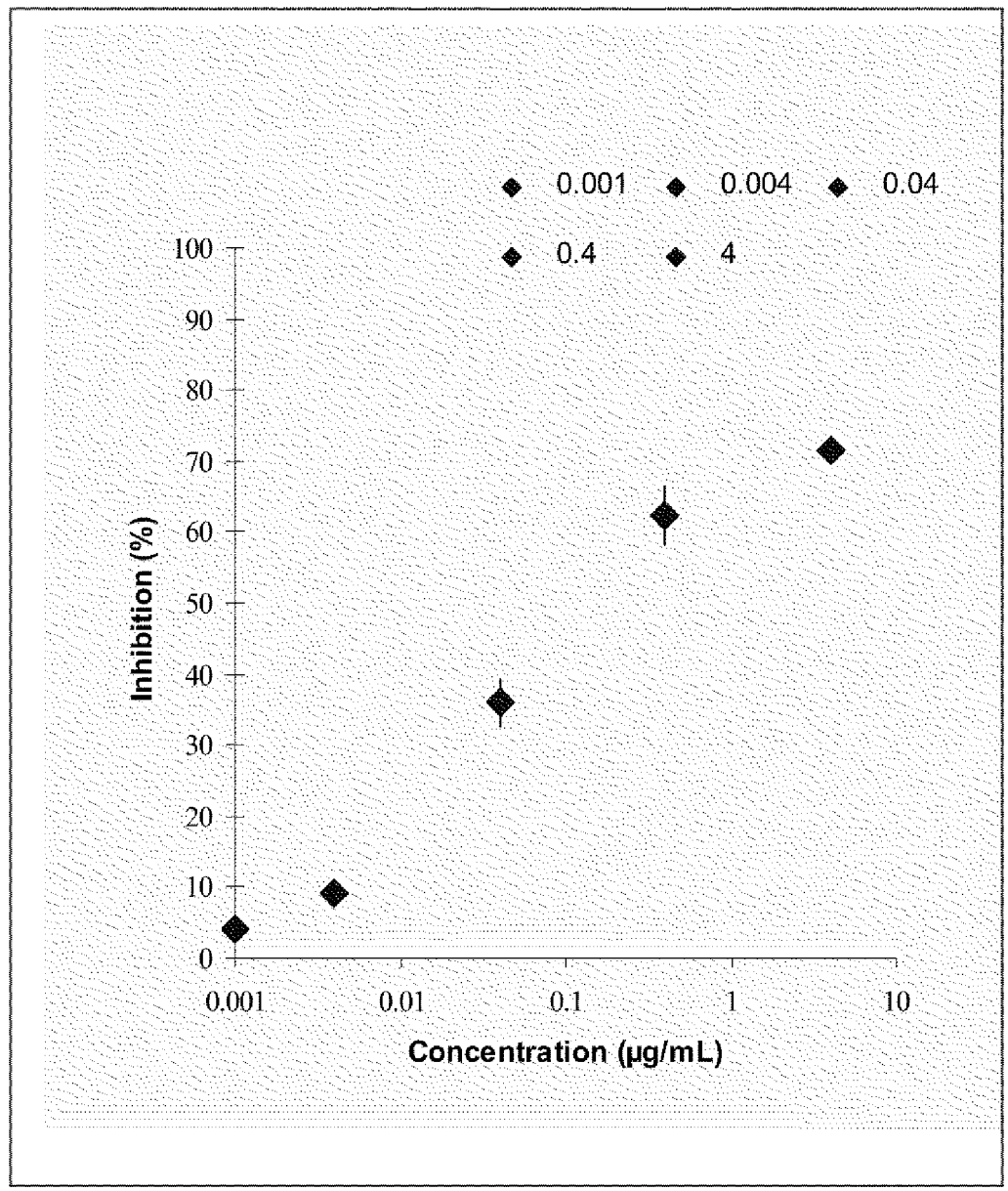
FIG. 9 graphically illustrates the percentage of inhibition by atrazine on stabilised thylakoid membranes determined with a specific embodiment of a fluorometer of the present invention and calculated with the data presented in FIG. 8.

Sensitivity of $F_1$ and $F_2$ Measures as Compared to Photosynthesis Efficiency to Measure Inhibition The ability of the measures $F_1$ and $F_2$ to provide accurate information on the presence of a toxic agent was compared to that provided by the formula $(F_2-F_1)/F_2(wi)$ (photosynthesis efficiency). The measures were performed on thylakoid membranes stabilised with PVP and liposomes as described herein. As is illustrated in FIG. 9, photosynthesis efficiency formula $(F_2-F_1)/F_2(wi)$ is more sensitive than $F_1$ and $F_2$ to evaluate the effect of inhibitors.

EXAMPLE 15

Influence of Physico-Chemical Parameters of Fluids Tested on Photosynthesis Efficiency of Stabilised Thylakoid Membranes

TABLE 10

Influence of some physico-chemical parameters on photosynthesis efficiency of stabilised thylakoid membranes

| Parameters (units) | Buffer 1 + 5 mM $MgCl_2$ in cuvette |
|---|---|
| Color (500 PtCo) | |
| Yellow and brown | No effect |
| Hardness (10-150 mg/L $CaCO_3$) | Increase of 15% |
| Dissolved oxygen (95%) | No effect |
| Conductivity (500 μS/cm) | No effect |
| Turbidity (NTU) | Increase of 15% |
| Suspended matter (2730 mg/L) | Increase of 15% |

Those are physico-chemical parameters that are usually tested to characterise water samples upon their reception. These parameters can lead to false results on toxicity evaluation.

In order to circumvent these eventual effects, it is suggested to read fluorescence values ($F_1$ and $F_2$)) at time zero and use them as blank (or zero value) in the calculation of the percentage of inhibition.

EXAMPLE 16

Effect of Temperature on Stabilised Thylakoid Membranes

Figure 10:
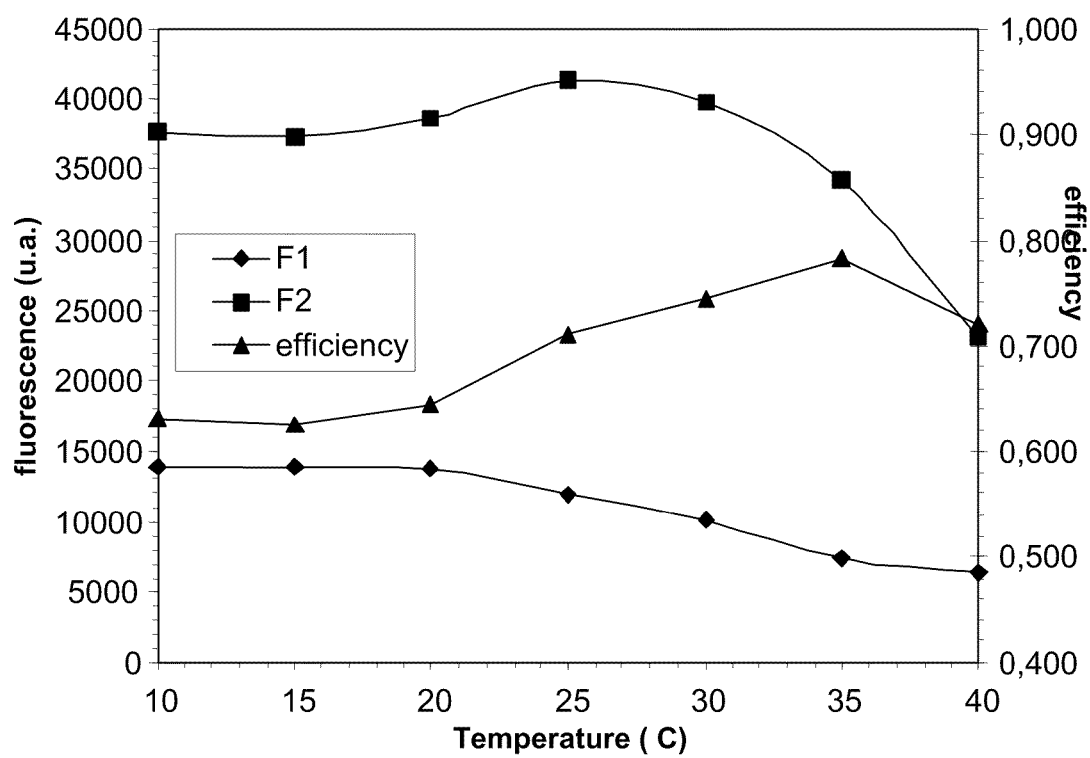
FIG. 10 graphically illustrates the variation of the photosynthetic efficiency of thylakoid membranes as a function of temperature.

The variation of the photosynthetic efficiency and fluorescence levels ($F_1$ and $F_2$) was measured on thylakoids stabilised with PVP and liposomes as described herein. The results presented in FIG. 10 indicate that the test can be conducted at temperature ranging from 4 to 35° C. if the readings of control and tested samples are made at the same temperature.

EXAMPLE 17

Determination of Spiked Atrazine in Water and Juice

Herbicides can also be detected in juices (after pH adjustment) or in water extracted from juices (gravimetric filtration)

as demonstrated in Table 11. The percentage of inhibition observed with weak atrazine concentrations in juices are similar to those observed in water.

TABLE 11

Determination of spiked atrazine in water and juice

| | Inhibition (%) | | | | |
|---|---|---|---|---|---|
| Atrazine (µg/mL) | Water | Commercial apple juice[1] | Commercial apple juice (clear)[1,2] | Commercial apple juice (with pulp)[1,2] | Biological apple juice |
| 0 | 0 | 0 | 0 | 0 | 0 |
| 0.01 | 16 | 11 | 15 | 23 | 23 |
| 0.1 | 60 | 61 | 60 | 58 | 61 |
| 4 | 80 | 84 | 74 | 65 | 71 |

[1]pH adjusted at 7
[2]gravimetric filtration, atrazine added before filtration

EXAMPLE 18

Toxicity Determination in Industrial Effluents

Figure 11:
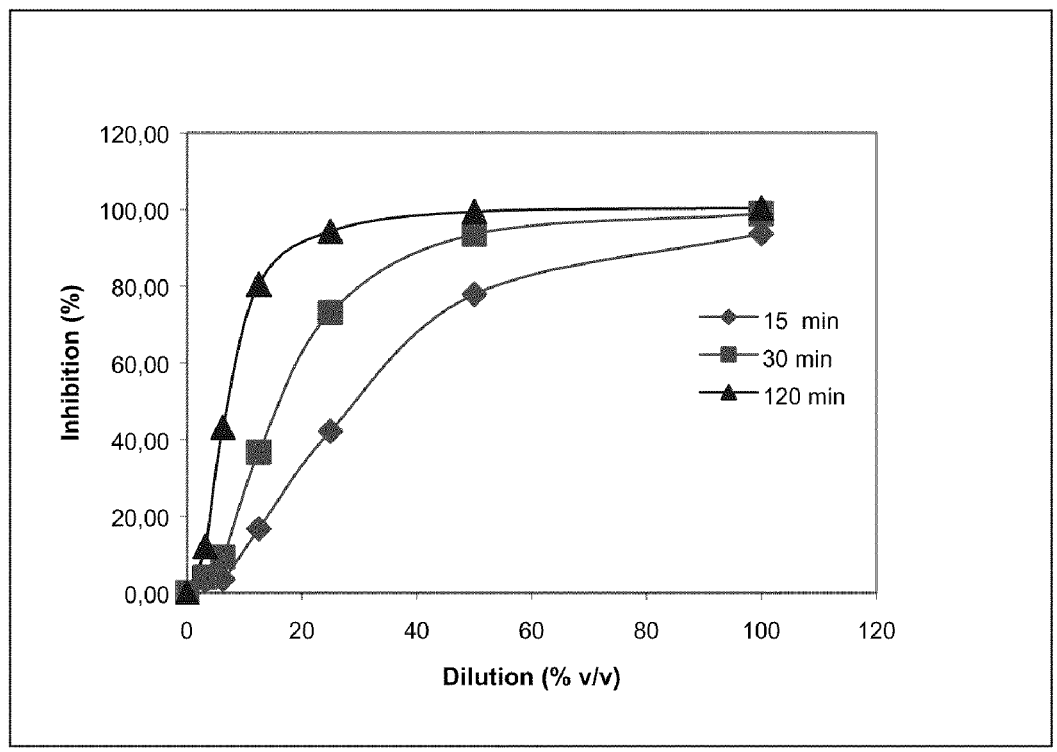
FIG. 11 graphically illustrates the percentage of inhibition by non treated (A) and treated (B) pulp and paper effluent on thylakoid membranes determined after different incubation times with a specific embodiment of a fluorometer of the present invention.
Figure 11:
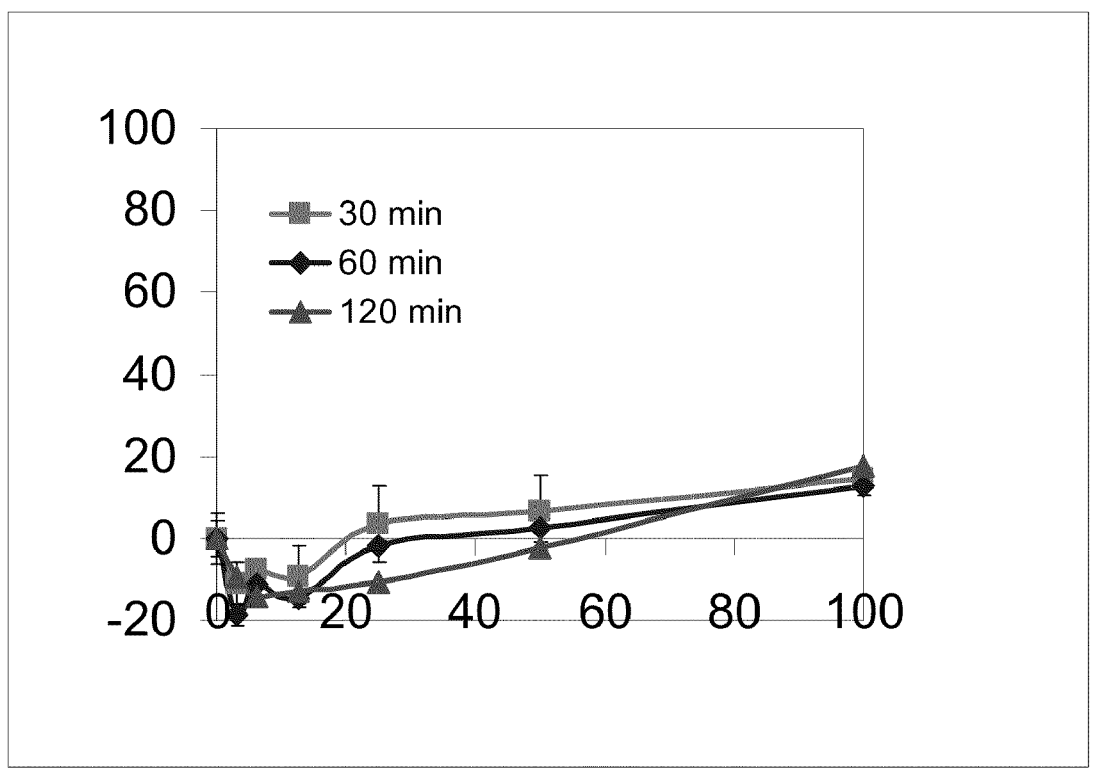
Figure 12:
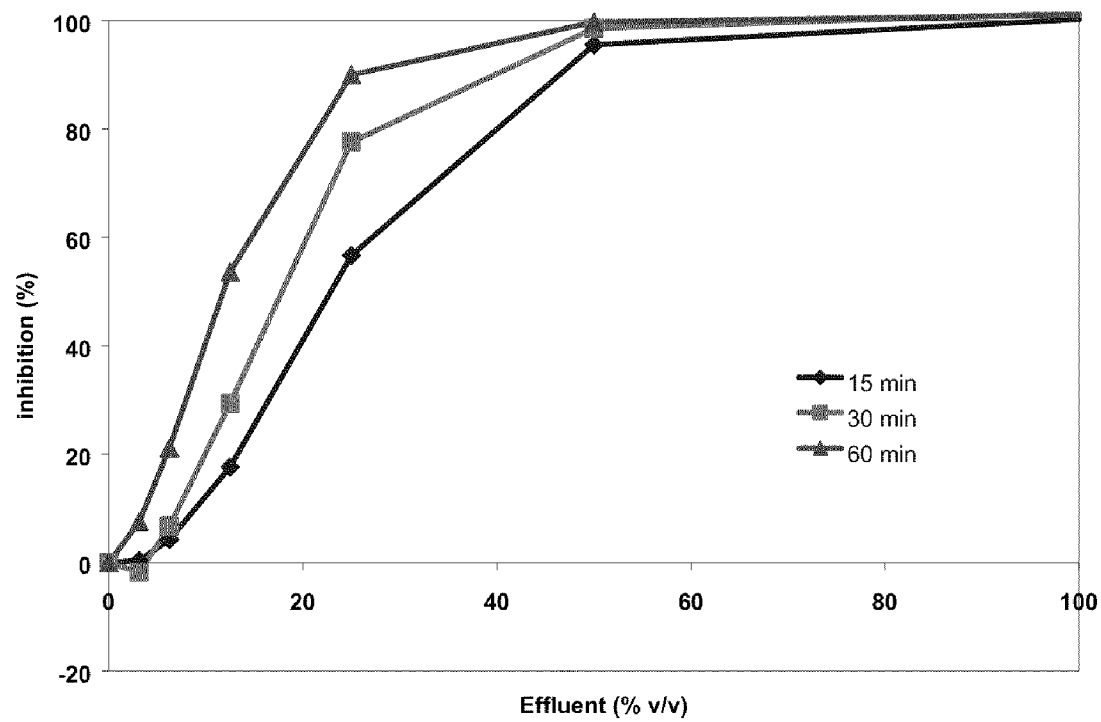
FIG. 12 graphically illustrates the percentage of inhibition by non treated (spontaneous P-D-L) (A) and treated (B) municipal waste water effluent on thylakoid membranes determined after different incubation times with a specific embodiment of a fluorometer of the present invention.
Figure 12:
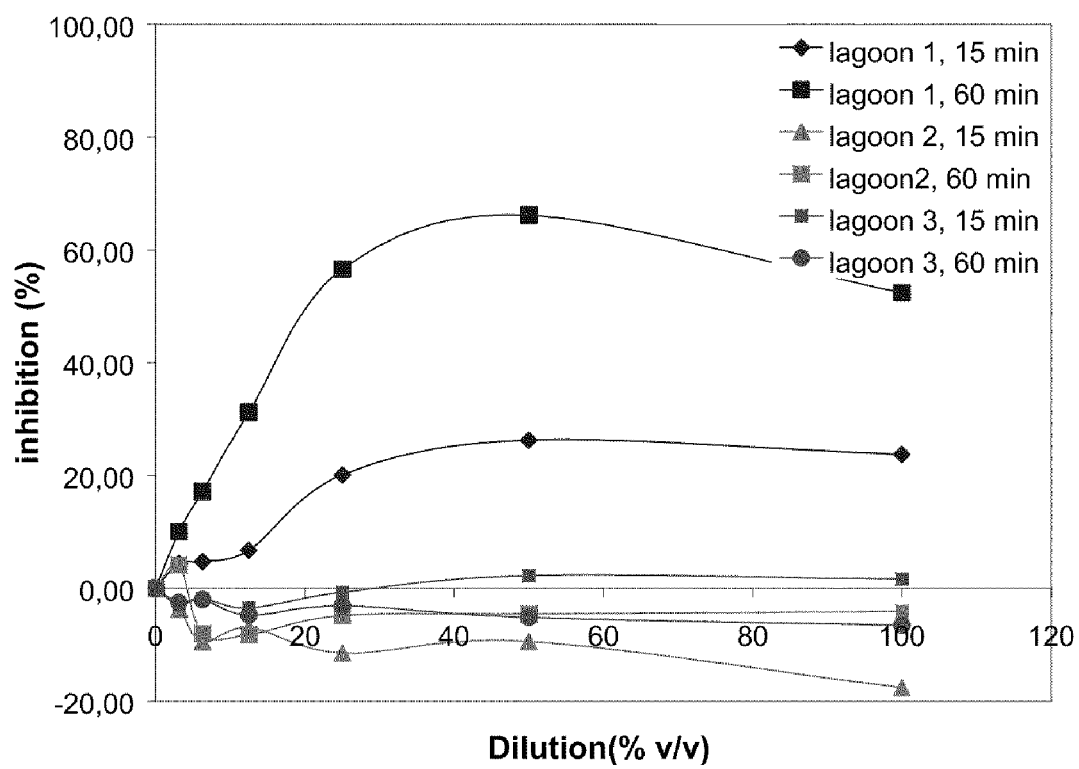
Figure 13:
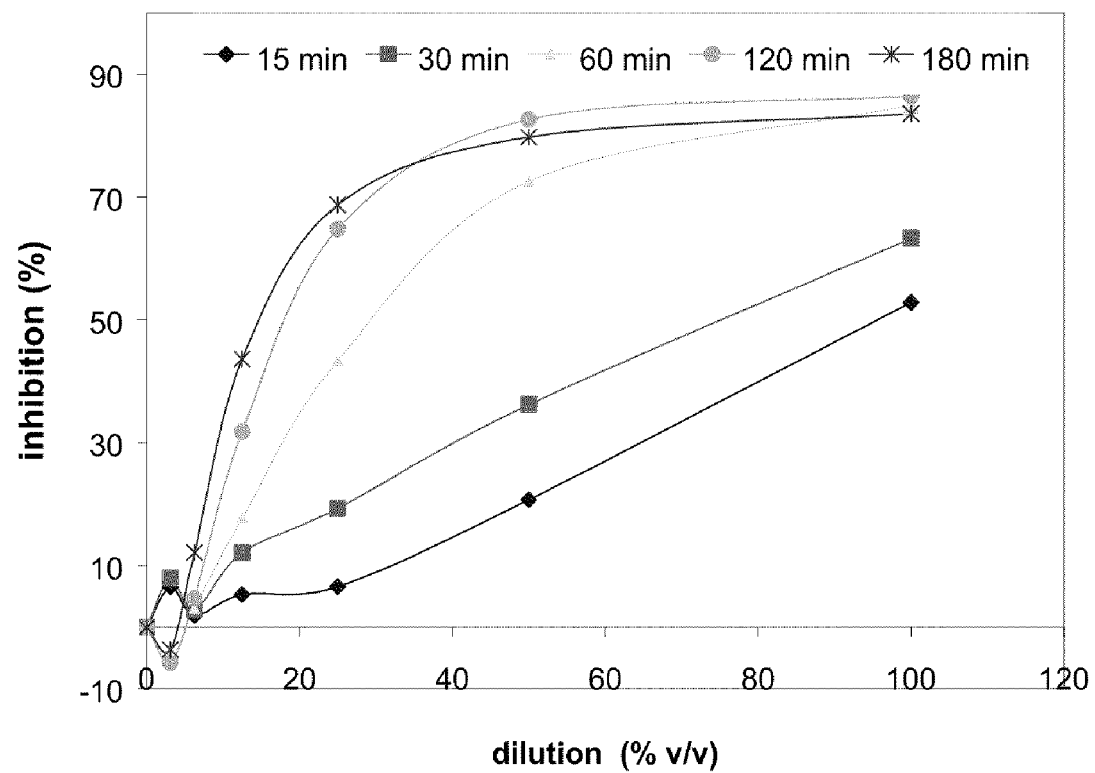
FIG. 13 graphically illustrates the percentage of inhibition by non-treated (A) and treated (UV treatment) (B) leachate effluent on thylakoid membranes determined after different incubation times with a specific embodiment of a fluorometer of the present invention.
Figure 13:
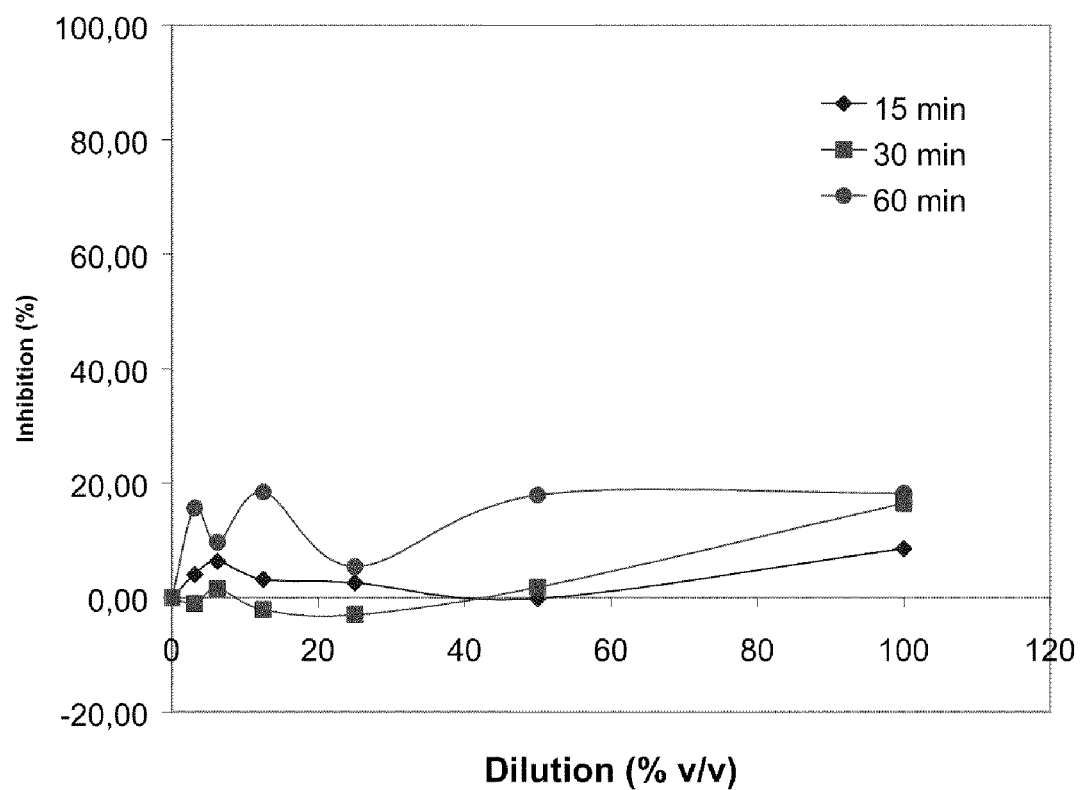

FIGS. 11 to 13 illustrate the efficiency of the test for toxicity determination in industrial effluents with different incubation times. The sensitivity of toxicity detection is enhanced by increasing incubation time in non-treated (non-treated=raw effluents, treated=biological, chemical or other treatments) effluents. Small concentrations of toxic molecules are detected in pulp and paper and leachate effluents even after 2 hours of incubation time. The test can be used to determine the efficiency of waste water treatments such as biological, aerobic or chemical treatments. FIGS. 11 to 13 show the efficiency of various such treatments (biological: pulp and paper industry (FIG. 11), aerobic treatment in municipal waste water (FIG. 12), an biological and chemical treatment in sanitary landfill site (FIG. 13).

EXAMPLE 19

Toxicity Determination in Environment Effluents

As may be seen in Table 12, some environmental toxic molecules that can be found in fluid samples may stimulate or inhibit photosynthetic efficiency.

Table 12 shows a short list of molecules detected by the present invention and their effects (inhibition or stimulation) on thylakoid membranes

| Toxic Molecules | Effect |
|---|---|
| Herbicides | Inhibition |
| Metal ions | Inhibition |
| $H_2O_2$ | Inhibition |
| NaCl | Stimulation |
| $CaCO_3$ | Stimulation |
| Nitrates | Weak inhibition |
| Phosphates | Stimulation |
| Oleic acid | Inhibition |
| Stearic acid | Stimulation |
| Ammoniacal nitrogen | Stimulation |
| Humic acid | Inhibition |

Although the present invention has been described herein above by way of preferred embodiments thereof, it can be modified, without departing from the spirit and nature of the subject invention as defined in the appended claims.

In particular, although examples presented herein show the use of stabilised thylakoid membranes preparations for detecting toxic molecule such as herbicides, metal ions, $H_2O_2$, NaCl, $CaCO_3$, nitrates, phosphates, oleic acid, stearic acid, ammoniacal nitrogen and humic acid, a person of ordinary skill in the art will understand that any toxic molecule able to disrupt the photosynthetic efficiency of thylakoid membranes may be detected according to the methods of the present invention.

REFERENCES

1. Conrad, R.; C. Büchel; C. Wilhelm; W. Arslane; C. Berkaloff and J.-C. Duval (1993). "Changes in yield of in-vivo fluorescence of chlorophyll as a tool for selective herbicide monitoring" *J. Appl. Phycol.* 5: 505-516;
2. Porra R. J., Thompson W. A., Kriedemann P. E., (1989) *Biochimia Biophysica Acta* 975: 384-394;
3. Ministère de l'Environnement du Québec (2001). *Critères de la qualité de l'eau de surface au Québec*. Direction des écosystèmes aquatiques, Ministère de l'Environnement, Québec;
4. Laberge, Chartrand, Rouillon, Carpentier (1999). "In vitro phytotoxicity screening test using immobilized spinach thylakoids" *Env. Tox. Chem.* 18 (12): 2851-2858;
5. Koblizek, Maly, Masojidek, Komenda, Kucera, Giardi, Mattoo, Pilloton (2002). "A Biosensor for the Detection of Triazine and Polylurea Herbicides Designed Using Photosystem II Coupled to a Screen-Printed Electrode" *Biotechnol. Bioeng.* 78 (1): 110-116;
6. Jay, Ducruet, Duval, Pelletier (1997). "A high-sensitive chlorophyll fluorescence assay for monitoring herbicide inhibition of photosystem II in the chlorophyte *Selenastrum capricornutum*": Comparison with effect on cell growth. *Arch. Hydrobiol.* 140 (2): 273-286;
7. Laberge, Rouillon, Carpentier (2000). "Comparative study of thylakoid membranes sensitivity for herbicide detection after physical or chemical immobilization" *Enz. Microb. Technol.* 26: 332-336;
8. Loranger, Carpentier (1994). "A fast bioassay for phytotoxicity measurements using immobilized photosynthetic membranes" *Biotech. Bioeng.* 44:1-5.
9. Rouillon, Carpentier (2000) "Amperometric activity measurements of photosynthetic material immobilized in poly (vinylalcohol)-SbQ Application to detect pollutants" *Curr. Topics Electroch.* 7: 125-133.
10. Finney, D. J. (1971), *Probit Analysis*, Cambridge University Press, 333 pages.

What is claimed is:

1. A stabilised thylakoid membrane formulation comprising thylakoid membranes in a buffered solution and liposomes, wherein the formulation has a ratio of chlorophyll/liposomes of at least about 10 mg $mL^{-1}$:1 mg $mL^{-1}$.

2. The formulation of claim 1, wherein the buffered solution has a pH between about 6.2 and about 7.8.

3. The formulation of claim 1, wherein the formulation has a ratio of chlorophyll/liposomes of between about 10 mg $mL^{-1}$:1 mg $mL^{-1}$ and 100 mg $mL^{-1}$:1 mg $mL^{-1}$.

4. The formulation of claim 1, further comprising polyvinylpyrrolidine (PVP) in a concentration lower than about 4% v/v.

5. The formulation of claim 1, wherein the liposomes are constituted of phosphatidylcholine and phosphatidylglycerol in a ratio of about 10 mg $mL^{-1}$:1 mg $mL^{-1}$.

6. A kit for detecting a toxic molecule in a fluid comprising:
(a) a stabilised thylakoids membranes formulation comprising thylakoids membranes in a buffered solution and liposomes, wherein the ratio of chlorophyll/liposomes is of at least about 10 mg mL$^{-1}$:1 mg mL$^{-1}$; and
(b) a portable fluorometer using non-modulated light.

7. The kit of claim 6, wherein the buffered solution has a pH between about 6.2 and about 7.8.

8. The kit of claim 6, further comprising polyvinylpyrrolidine (PVP) in a concentration lower than about 4% v/v.

9. The kit of claim 6, wherein the liposomes are constituted of phosphatidylcholine and phosphatidylglycerol in a ratio of about 10 mg mL$^{-1}$:1 mg mL$^{-1}$.

10. A method for detecting or quantifying the presence of toxic molecules in a fluid sample, comprising
obtaining the stabilised thylakoids membranes formulation of claim 1; and
assessing the photosynthetic efficiency of the thylakoid membranes formulation in the presence of said sample, whereby said molecules are detected when said photosynthetic efficiency is measurably different in the presence versus in the absence of said sample.

11. The method of claim 10, wherein the photosynthetic efficiency is assessed with a fluorometer using non-modulated light after the thylakoid membranes formulation has been incubated with the sample for a time sufficient to enable any toxic molecules in the sample to disrupt the photosynthetic efficiency of the thylakoid membranes formulation.

12. The method of claim 11, wherein the molecules comprise a herbicide and wherein the photosynthetic efficiency assessment is conducted after the thylakoid membranes formulation has been incubated for 10 minutes.

13. The method of claim 11, wherein the molecules comprise a metal ion and wherein the photosynthetic efficiency assessment is conducted after 15 to 180 minutes.

14. A method of stabilising thylakoid membranes for use in bioassays comprising mixing thylakoid membranes in a buffered solution with liposomes to yield a thylakoid membranes formulation, whereby the final ratio of chlorophyll/liposomes in the formulation is of at least about 10 mg mL−1:1 mg mL−1.

15. The method of claim 14, wherein the buffered solution has a pH between about 6.2 and about 7.8.

16. The method of claim 14, wherein the final ratio of chlorophyll/liposomes in the formulation is of between about 10 mg mL−1:1 mg mL−1 and 100 mg mL−1:1 mg mL−1.

17. The method of claim 14, wherein the formulation further comprises polyvinylpyrrolidine (PVP) in a concentration lower than about 4% v/v.

18. The method of claim 14, wherein the liposomes are constituted of phosphatidylcholine and phosphatidylglycerol in a ratio of about 10 mg mL−1:1 mg mL−1.

19. The method of claim 10, wherein the toxic molecule is selected from the group consisting of herbicides, metal ions, $H_2O_2$, NaCl, $CaCO_3$, nitrates, phosphates, oleic acid, stearic acid, ammoniacal nitrogen and humic acid.

* * * * *